(12) United States Patent
Richter et al.

(10) Patent No.: US 9,790,194 B2
(45) Date of Patent: Oct. 17, 2017

(54) PROCESS FOR CONTINUOUS ISOCYANATE MODIFICATION

(71) Applicant: Covestro Deutschland AG, Leverkusen (DE)

(72) Inventors: Frank Richter, Leverkusen (DE); Martin Anstock, Krefeld (DE); Philip Bahke, Houston, TX (US); Andreas Gosch, Bochum (DE); Reinhard Halpaap, Odenthal (DE); Andreas Hecking, Langenfeld (DE); Sigurd Buchholz, Köln (DE); Ursula Tracht, Leverkusen (DE); Adrian Cosmin Dobre, Köln (DE)

(73) Assignee: Covestro Deutschland AG, Leverkusen (DE)

( * ) Notice: Subject to any disclaimer, the term of this patent is extended or adjusted under 35 U.S.C. 154(b) by 576 days.

(21) Appl. No.: 14/360,727

(22) PCT Filed: Nov. 29, 2012

(86) PCT No.: PCT/EP2012/073998
§ 371 (c)(1),
(2) Date: May 27, 2014

(87) PCT Pub. No.: WO2013/079614
PCT Pub. Date: Jun. 6, 2013

(65) Prior Publication Data
US 2014/0343280 A1    Nov. 20, 2014

(30) Foreign Application Priority Data
Nov. 30, 2011   (EP) .................................... 11191377

(51) Int. Cl.
| | |
|---|---|
| *C07D 273/04* | (2006.01) |
| *C08G 18/78* | (2006.01) |
| *C08G 18/79* | (2006.01) |
| *C08G 18/09* | (2006.01) |
| *C08G 18/02* | (2006.01) |

(52) U.S. Cl.
CPC ......... *C07D 273/04* (2013.01); *C08G 18/022* (2013.01); *C08G 18/025* (2013.01); *C08G 18/092* (2013.01); *C08G 18/7831* (2013.01); *C08G 18/791* (2013.01)

(58) Field of Classification Search
CPC .. C07D 273/04; C08G 18/022; C08G 18/025; C08G 18/092; C08G 18/7831; C08G 18/791
See application file for complete search history.

(56) References Cited

U.S. PATENT DOCUMENTS

| | | | |
|---|---|---|---|
| 4,454,317 A | 6/1984 | Disteldorf et al. | |
| 4,960,848 A | 10/1990 | Scholl et al. | |
| 5,013,838 A | 5/1991 | Scholl | |
| 5,770,671 A | * 6/1998 | Nefzger | ............... C08G 18/10 528/56 |
| 5,914,383 A | 6/1999 | Richter et al. | |
| 6,107,484 A | 8/2000 | Richter et al. | |
| 8,445,622 B2 | 5/2013 | Binder et al. | |
| 2004/0106789 A1 | 6/2004 | Richter et al. | |
| 2005/0113551 A1 | 5/2005 | Richter et al. | |
| 2006/0079694 A1 | 4/2006 | Richter | |
| 2008/0262262 A1 | 10/2008 | Richter et al. | |
| 2009/0143558 A1 | 6/2009 | Richter et al. | |
| 2009/0234091 A1 | 9/2009 | Richter et al. | |
| 2011/0218314 A1 | 9/2011 | Kabir et al. | |

FOREIGN PATENT DOCUMENTS

| | | | |
|---|---|---|---|
| CA | 2244486 A1 | | 2/1999 |
| DE | 10232573 A1 | | 2/2004 |
| DE | 102004060131 | * | 6/2006 |
| DE | 102004060131 A1 | | 6/2006 |
| EP | 0017998 A1 | | 10/1980 |
| EP | 0235388 A2 | | 9/1987 |
| EP | 0295926 A2 | | 12/1988 |
| EP | 0315692 A1 | | 5/1989 |
| EP | 0339396 A1 | | 11/1989 |
| EP | 0379914 A2 | | 8/1990 |
| EP | 0447074 A2 | | 9/1991 |
| EP | 0798299 A1 | | 10/1997 |
| EP | 0896009 A1 | | 2/1999 |
| EP | 0962454 A1 | | 12/1999 |
| EP | 0962455 A1 | | 12/1999 |
| EP | 1422223 A1 | | 5/2004 |

(Continued)

OTHER PUBLICATIONS

English translation of DE102004060131, Jun. 2006, pp. 1-18.*
Laas et al., "The Synthesis of Aliphatic Poyisocyanates Containing Biuret, Isocyanurate or Uretdione Backbones for Use in Coatings", J. prakt. Chem. 336 (1994) pp. 185-200.
International Search Report for PCT/EP2012/073998, dated Dec. 5, 2013.
Laas, H.J., et al., "The Synthesis of Aliphatic Polyisocyanates Containing Biuret, Isocyanurate or Uretdione Backbones for Use in Coatings", Journal für praktische Chemie Chemiker-Zeitung, vol. 336, (1994), pp. 185-200.

*Primary Examiner* — Pancham Bakshi
*Assistant Examiner* — Mark Luderer
(74) *Attorney, Agent, or Firm* — John E. Mrozinski, Jr.

(57) ABSTRACT

A process for continuous preparation of oligomeric or polymeric isocyanates by catalytic modification of monomeric di- and/or triisocyanates, characterized in that at least one isocyanate component A and at least one catalyst component B are combined continuously in a reaction apparatus and conducted through the reaction apparatus as a reaction mixture, the residence time distribution being characterized according to the dispersion model by Bo (Bodenstein number) above 40, preferably above 60 and most preferably above 80.

14 Claims, 1 Drawing Sheet

(56) References Cited

FOREIGN PATENT DOCUMENTS

| | | |
|---|---|---|
| EP | 1533301 A2 | 5/2005 |
| EP | 1645577 A1 | 4/2006 |
| EP | 1861428 | 9/2006 |
| EP | 1982979 A1 | 10/2008 |
| EP | 2067773 A2 | 6/2009 |
| EP | 2100886 A2 | 9/2009 |
| WO | WO-2006/094706 A1 | 9/2006 |

* cited by examiner

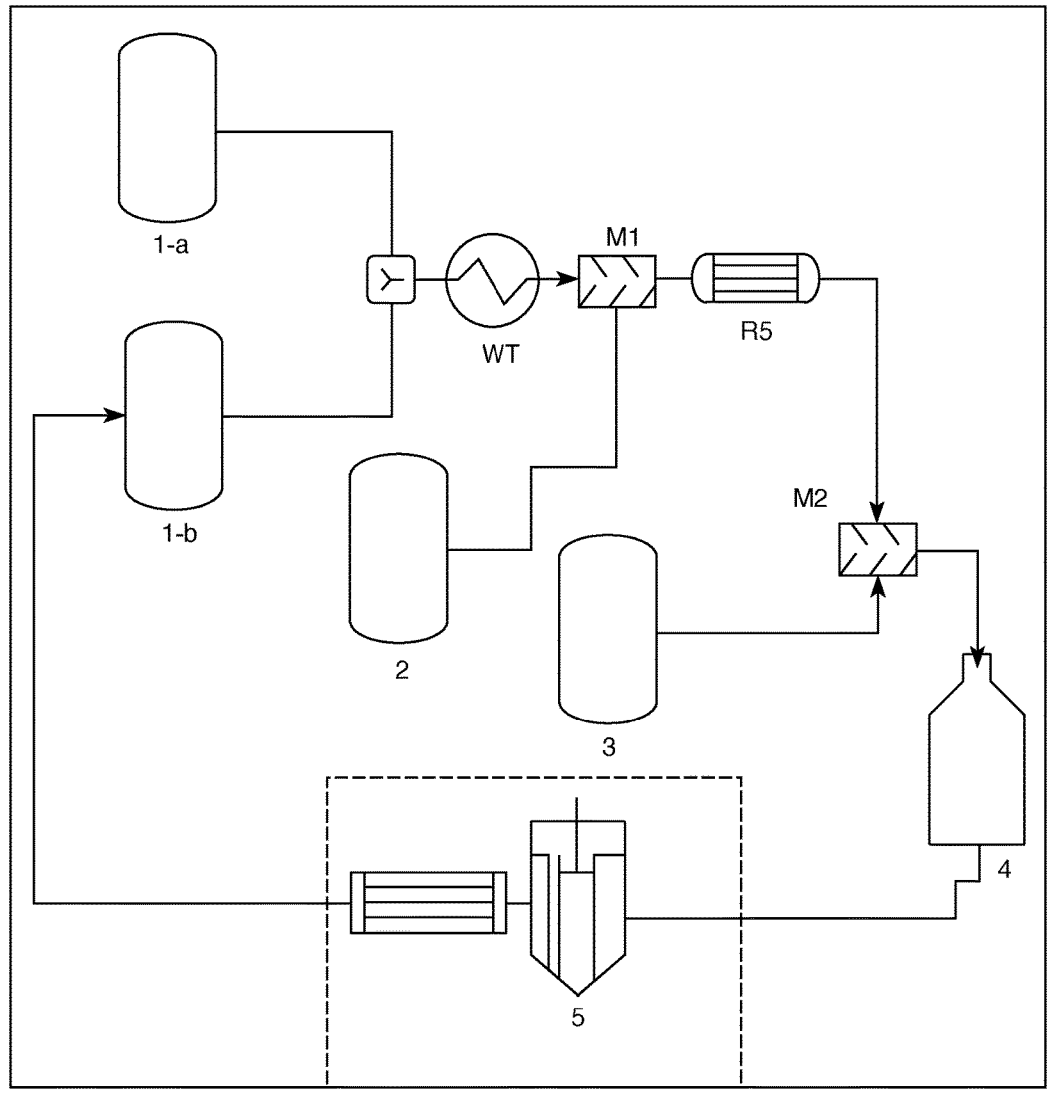

PROCESS FOR CONTINUOUS ISOCYANATE MODIFICATION

CROSS-REFERENCE TO RELATED APPLICATIONS

This application is a national stage application (under 35 U.S.C. §371) of PCT/EP2012/073998, filed Nov. 29, 2012, which claims benefit of European Application No. 11191377.8, filed Nov. 30, 2011, both of which are incorporated herein by reference in their entirety.

The oligomerization or polymerization of isocyanates, in particular diisocyanates, here referred to collectively as modification, has been known for a long time. If the modified polyisocyanates contain free NCO groups, which may also have been temporarily deactivated by means of blocking agents, they are extraordinarily valuable starting materials for producing many polyurethane plastics and coating compositions.

A number of industrial processes for isocyanate modification have become established; in these, the isocyanate to be modified, usually a diisocyanate, is generally reacted by addition of catalysts and is subsequently, when the desired degree of conversion of the isocyanate to be modified has been reached, made inactive (deactivated or separated off) by means of suitable measures and the polyisocyanate obtained is generally separated off subsequently or simultaneously from unreacted monomers. The latter is usually effected by distillation. The monomer recovered by distillation (generally the starting isocyanate) is subsequently reacted again in the same way. A compilation of these processes of the prior art may be found in H. J. Laas et al., J. Prakt. Chem. 1994, 336, 185 ff.

Specific forms of isocyanate modification are dimerization and trimerization, with only one isocyanate dimer (uretdione) but two groups of isocyanate trimers being known: isocyanurates and iminooxadiazinediones (sometimes also referred to as unsymmetric trimers or asymmetric trimers). Compared to the isomeric isocyanurates (on the basis of the same starting material), iminooxadiazinediones have largely identical properties such as molecular weight (distribution) and NCO content but a significantly lower viscosity and are therefore particularly suitable for producing low-solvent and solvent-free polyisocyanates, in particular for the surface coatings raw materials and coating compositions sector. Even when the polyisocyanates formed by diisocyanate "trimerization" contain not only the molecules having only one isocyanurate or iminooxadiazinedione ring ("ideal structure", n=3, where n in the text denotes the number of monomeric diisocyanate units built into the respective oligomer molecule) but also higher molecular weight components (n=5, 7, 9, etc.) in which both structure types (isocyanurates and iminooxadiazinediones) may also be present, these oligomer mixtures are generally referred to here as simply "isocyanate trimers". A corresponding situation applies to uretdione formation ("dimerization"). Small proportions of oligomer constituents bearing uretdione groups are generally always obtained in the trimerization, and conversely isocyanate dimerization is difficult to carry out so that no isocyanate trimers are formed. The designation of the process products as "trimer" (optionally with the prefix "asymmetric") vs. "dimer" is thus always based on the type of structure types which are predominant in the oligomer mixture, which can easily be determined by means of IR and/or NMR spectroscopy or other analytical methods.

A series of compounds have been found to be useful as catalysts for the modification of isocyanates, cf. H. J. Laas et al., J. Prakt. Chem. 1994, 336, 185 ff, EP 2100886, EP 2067773, EP 1982979; EP 1645577; EP 1533301, EP 1422223, EP 962455, EP 962454, EP 896009, EP 798299, EP 447074, EP 379914, EP 339396, EP 315692, EP 295926 and EP 235388.

Substances having a covalent structure with trivalent phosphorus as central atom which is not part of a ring and also particular aminopyridines are particularly suitable for dimerization.

Specific phosphacycles having a trivalent P atom and substances having a salt-like structure with cations which ensure good solubility in the isocyanate medium, in particular tetraorganylammonium and tetraorganylphosphonium, and anions which are derived by $H^+$ abstraction from weak acids such as carboxylic acids, phenols, alcohols, water, HF, etc., are particularly suitable for trimerization. Fluorides, hydrogendifluorides, dihydrogentrifluorides and higher polyfluids and also the anions of specific carboxylic acids bearing fluorinated alkyl groups lead to increased formation of isocyanate trimers having a high iminooxadiazinedione group content.

A disadvantage of these processes of the prior art is that the species used as catalyst frequently decompose to form interfering by-products, which in the case of the ammonium salts is, undesirably, made noticeable by the presence of tertiary amines in the process products, which can be revealed, for example, by an unpleasant amine odor of the polyisocyanates and problems in respect of the long-term stability of such problems and in the case of the phosphonium salts is revealed by a gradually increasing phosphorus content of the recovered (generally by distillation) monomer (recycled material), which has an adverse effect on process stability.

Although distillate streams which are contaminated in this way can be purified, cf. EP 1939171, such a procedure is associated with an additional outlay which is to be avoided.

These negative accompanying phenomena occur to an increased extent in continuous isocyanate modification, e.g. in a multivessel cascade, since here, due to short residence times and/or relatively high reaction temperatures, larger amounts of catalyst (based on the isocyanate to be modified) generally have to be employed compared to the discontinuous ("batch") mode of operation.

In addition, in the case of a continuous reaction, a broader molecular weight distribution of the process products, which is reflected in a higher viscosity and a lower isocyanate content of the polyisocyanates and in turn results in decreased conversions compared to the discontinuous ("batch") process, so that the preparation of polyisocyanates having identical product properties (in particular viscosity and NCO content) is desirable, frequently has to be accepted.

If highly diluted catalyst solutions in catalyst solvents which are reactive toward isocyanates, typically monofunctional, bifunctional or, less commonly, trifunctional alcohols, are used, there is a further problem: although the intended (main) reaction, viz. isocyanate modification, can be terminated at lower conversions by stopping the reaction early, the reaction of the catalyst solvents with the free isocyanate groups of all species present in the reaction mixture cannot; this always proceeds at least to the stage of the urethane (carbamate), but it is generally undesirable to continue the reaction of the alcohol to the state of the allophanate, which requires the presence of the active trimerization catalyst which is generally also suitable and necessary for allophanate formation. Compared to the urethanes built up from the same building blocks, allophanates are more readily soluble in the polyisocyanate than the corresponding urethanes and have, at least in the case of the products based on monofunctional alcohols, a significantly lower viscosity than the trimers. On the other hand, it is in principle disadvantageous that the allophanates derived from monofunctional alcohols and diisocyanates are only NCO-bifunctional and thus reduce the (average) NCO-functionality of the polyisocyanates.

Continuous processes are not new in polymer chemistry, cf. EP 1861428 and prior art cited therein. However, the teaching of EP 1861428 gives no pointer to carrying out the specific process of isocyanate oligomerization. Thus, EP 1861428 speaks quite generally of mixing at least two solutions containing the reactants. Apart from the abovementioned reaction of the catalyst solvent which proceeds to a minor extent if the solvent contains any NCO-reactive functional groups at all, isocyanate modification is characterized by the reaction of only one reactant. Furthermore, according to the teaching of EP 1861428, the reaction is carried out in the presence of ultrasound which comes up against significant difficulties in the industrial implementation of the process as the plant size increases.

A continuous process is indicated quite generally as a suitable embodiment of the process in many patent texts on (di)isocyanate modification, but without specific indications of the solution of the abovementioned problems being given.

In particular, DE 10232573 describes a process for the continuous preparation of polyisocyanates which contain isocyanurate groups and have aromatically bonded isocyanate groups, in which the reaction is said to be carried out in tube reactors having turbulent flow at Reynolds numbers above 2300 or in reactors having mixing elements at a power input above 0.2 W/l. This procedure has the following disadvantages:

the required high Reynolds number necessitates a high throughput in the tube reactor and when the viscosity increases, as is inevitably the case with increasing conversion in (di)isocyanate trimerization, generally demands an increase in the reaction temperature in order to satisfy the turbulence criterion. The reaction therefore cannot be scaled at will either in the direction of lower product throughputs or in the direction of lower reaction temperatures which are, in particular, constant over the entire reaction distance and would then lead, when the Reynolds number goes below that required for turbulence (whether throughput-related or temperature-related), to products having a significantly broadened molecular weight distribution compared to the batch process.

Reactions in reactors having mixing elements are described in DE 10232573 [0016], in particular for the example of stirred cell reactors. These always have backmixing which is not negligible, especially in the case of low power input via the mixing element, which is why DE 10232573 [0014] explicitly discusses the power input (above 0.2 W/l, preferably above 0.3 W/l, particularly preferably 0.5 W/l and very particularly preferably 0.8 W/l). Such a dependence of the result of the modification reaction on the power input is generally disadvantageous.

The reaction of aliphatic isocyanates is not described.

Recirculation of unreacted monomer after partial conversion of the monomers is not described, and no information on the behavior of the catalyst downstream and decomposition products in a process having only partial monomer conversion and subsequent recovery of the monomer could therefore be derived from the teaching of DE 10232573.

EP 17998 refers, inter alia, to carrying out the trimerization in a "coolable, tubular reactor with simultaneous introduction of catalyst-containing monomeric isocyanate" (EP 17998, claim 3). However, introduction of a previously made mixture of catalyst and isocyanate to be trimerized is generally disadvantageous and succeeds only when either isocyanates having a low reactivity, e.g. cycloaliphatics or sterically hindered linear aliphatics are used, which EP 17998 does not do in the major part of the examples, or when the catalyst does not bring about the (strongly exothermic) trimerization immediately after addition to the isocyanate but instead displays a certain latent time. Both impose a severe restriction on the process described in EP 17998. In addition, as can be seen from the examples in EP 17998, the isocyanate-catalyst mixture is trimerized to an extent of 7.5-10% even before entry into the reaction section. Low conversions, which are frequently preferred nowadays since they lead to low-viscosity products and which are becoming important in view of ever stricter requirements in terms of prevention of emissions (keyword: VOC), therefore cannot be achieved by the methods described in the prior art.

In addition, as can be seen from the examples in EP 17998 which relate to the continuous trimerization of hexamethylene diisocyanate (HDI) (EP 17998, examples B4, B5 and B6, see also table IIa there), the molecular weight distribution of the products obtained has to be significantly broader than it would have been in a batch experiment at comparable conversion, characterized by the refractive index of the crude product before removal of the monomer by distillation: none of the examples given in EP 17998 for HDI trimers gives products having an NCO content above 21.4%, see also the comparative examples of the present text.

Finally, DE 10 2004 06 0131 claims a continuous process for the partial trimerization of (cyclo)aliphatic isocyanates in the presence of at least one catalyst, characterized in that the process is at least partly carried out in at least two backmixed reaction zones. Such a procedure is generally disadvantageous for obtaining polyisocyanates having a narrow molecular weight distribution.

US 2011/0218314 claims a continuous process for the catalytic oligomerization of isocyanates to form carbamate (urethane) or allophanate groups. Quaternary ammonium hydroxides are used as catalysts. Reference is made to an extremely high heat transfer coefficient in order to achieve better temperature control within the reactor and associated better control of the oligomerization reaction. Disadvantages of the apparatuses having such high heat transfer coefficients which are used here are firstly the high pressure drop and secondly the extremely unfavorable geometry which results in a high susceptibility to phenomena which frequently occur in isocyanate chemistry in particular, e.g. spontaneous formation of gel particles, viscosity increases, etc.

It was an object of the present invention to provide a process for the continuous preparation of polyisocyanates which does not suffer from the abovementioned disadvantages: the catalysts should not have a tendency to decompose with formation of interfering secondary components which could accumulate in the process products or have a lower such tendency compared to processes of the prior art. They should lead, even when used in dilute alcoholic solution, to batch-type products, i.e. the molar ratio of the pure isocyanate oligomers (isocyanurates and/or iminooxadiazindiones and to a lesser extent also uretdiones) to the products from NCO—OH reactions (urethanes and allophanates)

should be in the range known from batch experiments. Compared to a discontinuous reaction with a similar degree of conversion of the monomer, the process products should have a similar molar mass distribution and, associated therewith, a similar viscosity and a similar NCO content.

This has been successfully achieved by provision of the process of the invention.

The invention provides a process for the continuous preparation of oligomeric or polymeric isocyanates by catalytic modification of monomeric diisocyanates and/or triisocyanates, characterized in that at least one isocyanate component and at least one catalyst component are continuously combined in a reaction apparatus and conveyed as reaction mixture through the reaction apparatus, where the residence time distribution according to the dispersion model is characterized by a Bo (Bodenstein number) above 40, preferably above 60 and very particularly preferably above 80.

None of the abovementioned documents of the prior art indicates that a reaction in continuously operated process-intensive apparatuses using catalyst concentrations comparable to or lower than those in the batch process makes it possible to produce products having similar viscosities and NCO contents without a decrease in conversion.

For the purposes of the present invention, continuous reactions are reactions in which the introduction of the starting materials into the reactor and the discharge of the products from the reactor take place simultaneously but physically separately. In the case of a discontinuous reaction, on the other hand, the reaction sequence, viz. introduction of the starting materials, chemical reaction and discharge of the products, occurs successively over time.

The continuous mode of operation is economically advantageous since times in which the reactor is not available for carrying out the reaction as a result of filling and emptying processes and long reaction times due to safety requirements, reactor-specific heat transfer performance and also heating and cooling processes as occur in batch processes are avoided.

The continuous reaction is, in a preferred embodiment, carried out using a residence section in the pressure range ≤30 bar, preferably ≤10 bar, particularly preferably in the range ≤4 bar.

The rates at which all components are introduced depend first and foremost on the desired residence times or conversions to be achieved. The residence time is, inter alia, set via the volume flows and the volume of the reaction zone. The higher the maximum reaction temperature, the shorter should the residence time be. In general, the residence times in the reaction zone are in the range from 20 seconds (20 sec) to 120 minutes (120 min), preferably from 90 sec to 90 min, very particularly preferably from 5 min to 60 min.

The course of the reaction is advantageously monitored by means of various measurement devices. Devices suitable for this purpose are, in particular, devices for measuring the temperature, the viscosity, the refractive index and/or the thermal conductivity in flowing media and/or for measuring infrared and/or near infrared spectra.

The reaction sections to be used according to the invention preferably have a suitable heat transfer performance which is characterized by the specific heat transfer rate in $W/(K\ m^3)$, i.e. heat transfer per kelvin temperature difference from the heat transfer medium based on the free volume of the reactor. In a preferred embodiment, the reaction sections to be used according to the invention are accordingly characterized in that, as a result of their structure in the process of the invention, they make a) a maximum pressure drop of from 0 to 30 bar, preferably from 0 to 10 bar and particularly preferably from 0 to 4 bar, possible and b) make a heat transfer rate above $10\ kW/(K\ m^3)$, preferably above $50\ kW/(K\ m^3)$ and particularly preferably above $100\ kW/(K\ m^3)$, possible.

Here, for example, the use of microreaction technology (µ-reaction technology) using microreactors is possible. The term "microreactor" used refers to microstructured, preferably continuously operated reactors which are known under the names mikroreactor, minireactor, microheat exchanger, minimixers or micromixers. Examples are microreactors, microheat exchangers, T- and Y-mixers and also micromixers from a variety of companies, (e.g. Ehrfeld Mikrotechnik BTS GmbH, Institut für Mikrotechnik Mainz GmbH, Siemens AG, CPC-Cellulare Process Chemistry Systems GmbH, and others), as are generally known to those skilled in the art, with, for the purposes of the present invention, a "microreactor" usually having characteristic, determining internal dimensions of up to 1 mm and being able to contain static mixing internals.

Intensive heat exchangers, e.g. CSE-XR types from Fluitec are likewise suitable, as long as they can satisfy the abovementioned properties in respect of their heat transfer properties. Combinations of microreactors with other larger heat exchangers, e.g. from Fluitec or Sulzer, are likewise conceivable. The essential feature of these combinations is the arrangement of the individual types of reactor in accordance with the expected, necessary heat transfer performance of the individual apparatuses taking into account the viscosities and pressure drops which occur.

To enable polyisocyanates having the desired product properties to be prepared, a narrow residence time distribution in the reactor system is of critical importance. The Bodenstein number Bo, as a measure of the breadth of the residence time distribution according to the dispersion model, is above 40, preferably above 60 and very particularly preferably above 80.

The narrow residence time distribution is usually achieved by the use of static mixing elements or of µ-reactors, as described above. Intensive heat exchangers, e.g. the CSE-XR type, typically likewise meet this requirement satisfactorily.

The components are generally introduced in separate feed streams into the reactor. In the case of more than two feed streams, these can also be fed in bonded together. It is also possible to additionally add catalysts and/or auxiliaries such as fluidizers, stabilizers or bonding agents to this product stream.

It is possible to introduce streams into the reactor in different proportions at various places in order to deliberately set concentration gradients, e.g. to bring about completion of the reaction. The entry position of the streams in the sequence can be made variable and offset in time. For prereaction and/or completion of the reaction, a plurality of reactors can be combined. To stop the reaction at the desired degree of conversion, further components can be introduced subsequent to the reaction section.

Individual streams or all streams can, before being combined, be brought to the desired temperature by means of a heat exchanger, i.e. brought to a temperature of from −20° C. to +200° C., preferably from +20° C. to +180° C., particularly preferably from +40° C. to +120° C. They are subsequently mixed by means of an intensive mixer and conveyed through one or more reactors. The components are preferably combined using mixing elements which bring about intensive mixing of the reactants. It is advantageous to use an intensive mixer (µ-mixer) by means of which the reaction solutions are, despite different volume flows and possibly also differing viscosity, mixed very quickly with one another, as a result of which a possible radial concentration gradient is avoided. After combining/mixing of the reactants, these are conveyed through the reaction apparatus which optionally contains further mixing elements. Further mixing elements along the reaction section lead to a preferred narrower residence time distribution. The reaction apparatus is characterized in that it makes available a residence time of from at least 20 sec to 120 min. All reactors are advantageously provided with a cooling and/or heating device, e.g. a jacket through which a temperature-controlled heat transfer fluid is passed.

The use of a plurality of independently heatable/coolable heating/cooling zones makes it possible, for example, to cool the flowing reaction mixture at the beginning of the reaction, i.e. shortly after mixing, and remove heat of reaction liberated and to heat the flowing reaction mixture toward the end of the reaction, i.e. shortly before discharge from the reactor, so that the residence time necessary for the desired conversion can be kept very small. The cooling medium and heating medium temperature can be in the range from −20 to +250° C.

The modification process of the invention has therefore made available an improved method of preparing isocyanate trimers continuously.

The process of the invention can be carried out in the temperature range from 0° C. to +200° C., preferably from 20° C. to 180° C., particularly preferably from 40° C. to 120° C., with a constant reaction temperature preferably being realized over the entire conversion range, and be stopped at desired degrees of conversion, preferably after from 5 to 80%, particularly preferably from 10 to 60%, very particularly preferably from 10 to 45%, of the monomeric diisocyanate used has been reacted. The unreacted monomer is subsequently recovered and used again in the process of the invention, with or without addition of fresh monomer and/or other auxiliaries and additives.

Possible catalysts are in principle all compounds which have previously been described for this purpose in the prior art as such or in, optionally highly diluted, solution. Particularly suitable catalysts appear to be salt-like substances having cations which ensure good solubility in the isocyanate medium, in particular tetraorganylammonium and tetraorganylphosphonium, and anions which are derived by H$^+$ abstraction from weak acids such as carboxylic acids, phenols, alcohols, water, HF, etc. Fluorides, hydrogendifluorides, dihydrogentrifluorides and higher polyfluorides and also the anions of specific carboxylic acids bearing fluorinated alkyl groups lead to increased formation of isocyanate trimers having a high iminooxadiazinedione group content.

Further suitable trimerization catalysts are alcoholic solutions of alkali metal and alkaline earth metal oxides, hydroxides, alkoxides and phenoxides. Alcoholic solutions of metal salts of carboxylic acids, for example potassium acetate, sodium benzoate, sodium acetate and potassium formate, and also tertiary phospines, in particular those which contain the phosphorus atom as part of a ring, are also suitable.

The following catalysts can preferably be used for the process of the invention: quaternary ammonium hydroxides, preferably N,N,N-trimethyl-N-benzylammonium hydroxide and N,N,N-trimethyl-N-(2-hydroxypropyl)ammonium hydroxide. Quaternary ammonium and phosphonium fluorides, difluorides, trifluorides and higher polyfluorides, as can be prepared by simple mixing of quaternary ammonium or phosphonium fluorides or hydroxides with appropriate proportions of HF, optionally predissolved in alcohols or water.

The type of trimerization catalyst plays a role in carrying out the process of the invention insofar as it significantly influences the product selectivity in respect of the formation of products containing predominantly uretdione, isocyanurate and/or iminooxadiazinedione groups. In particular, small proportions which can nevertheless be set in a targeted manner of oligomer constituents bearing uretdione groups in oligomer mixtures which are otherwise predominantly composed of the two isocyanate trimer structures can optionally be implemented by selection of the catalyst and the reaction conditions, which is expressly included in the scope of the process of the invention.

The catalyst requirement in the process of the invention is not above that in the bulk modification of the prior art (discontinuous "batch" process) and is frequently even lower. This is particularly surprising and could not have been expected.

The catalyst can, for example, be used in a proportion in the range from 1 mol-ppm and 1 mol %, preferably in the range from 5 mol-ppm to 0.1 mol %, based on the mass of monomer used. The amount of catalyst is a further parameter for setting the required residence time. In the process of the invention, good temperature control is achieved without problems even at high catalyst concentrations, so that significantly shorter residence times than in the established discontinuous batch process are possible.

An entire series of previously described methods of the prior art are in principle possible for deactivating the catalyst, e.g. the addition of substoichiometric or superstoichiometric amounts (based on the catalyst used) of acids (e.g. acids containing HCl, phosphorus or sulfur, but not HF) or acid derivatives (e.g. acid chlorides, acidic esters of acids containing phosphorus or sulfur, etc.). Further suitable methods of deactivating the catalyst are alkylating agents when trivalent phosphorus compounds are used as catalysts, adsorptive binding of the catalyst and subsequent removal by filtration, thermal deactivation, recovery by distillation, preferably together with the unreacted monomer to be recirculated, extraction, etc.

The low-monomer isocyanate trimers resulting from the process of the invention have at least the same, high quality level as the products obtained by the previously described processes of the prior art and cannot be distinguished analytically therefrom. The amine odor of the process products which is sometimes perceptible when catalysts having quaternary ammonium salts based on, in particular short-chain, alkyl or aralkyl substituents on the nitrogen atom are used is significantly reduced or eliminated. Contamination of the recycled monomer with P-containing substances when catalysts comprising phosphonium cations are used for the catalysis is likewise significantly reduced.

If the process products are polyisocyanates ("trimers") of the iminooxadiazinedione type, the proportion of iminooxadiazinedione groups, based on the total amount of subsequent products formed by the modification reaction from previously free NCO groups, is preferably above 30 mol %, particularly preferably above 40 mol %, where the balance to 100% can be attributed essentially to isocyanurate groups. The uretdione content of these specific process products is below 2/mol %, preferably below 10 mol %.

To carry out the process of the invention, it is in principle possible to use all known (di)isocyanates of the prior art either individually or in any mixtures with one another.

In particular, mention may be made of: pentane 1,5-diisocyanate, hexamethylene diisocyanate (HDI), 2-methylpentane 1,5-diisocyanate, 2,4,4-trimethylhexane 1,6-diisocyanate, 2,2,4-trimethylhexane 1,6-diisocyanate, 4-isocyanatomethyloctane 1,8-diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl) cyclohexane (H6XDI).

Furthermore, aromatic isocyanates such as tolylene 2,4- and 2,6-diisocyanate (TDI), bis(4-isocyanatophenyl)methane (4,4'-MDI), 4-isocyanatophenyl-2-isocyanatophenylmethane (2,4'-MDI) and also multiring products which can be obtained by formaldehyde-aniline polycondensation and subsequent conversion of the resulting (poly)amines into the corresponding (poly)isocyanates (polymeric MDI) can be used in the process of the invention.

Preference is given to aliphatic diisocyanates and/or triisocyanates, particularly preferably aliphatic diisocyanates, very particularly preferably hexamethylene diisocyanate (HDI), 2-methylpentane 1,5-diisocyanate, 2,4,4-trimethylhexane 1,6-diisocyanate, 2,2,4-trimethylhexane 1,6-diisocyanate, 4-isocyanatomethyloctane 1,8-diisocyanate, even more preferably HDI.

Here, which process is used for generating the abovementioned diisocyanates and (poly)isocyanates, i.e. with or without use of phosgene, is inconsequential.

The products or product mixtures obtainable by the process of the invention are thus versatile starting materials for producing, optionally foamed, plastics and also surface coatings, coating compositions, adhesives and auxiliaries. They are particularly suitable for producing, optionally water-dispersible, one-component and two-component polyurethane coating compositions, optionally in NCO-blocked form, owing to their solution viscosity or melt viscosity which is reduced compared to (predominantly) isocyanurate-polyisocyanate-based products while maintaining an otherwise equally high or improved property profile. Thus, the process products of the invention based on HDI are, even in high dilution in surface coating solvents, more stable to the occurrence of flocculation and turbidity than corresponding products based on isocyanurate.

They can be used in pure form or in combination with other isocyanate derivatives of the prior art, e.g. polyisocyanates which contain uretdione, biuret, allophanate, isocyanurate and/or urethane groups and whose free NCO groups have optionally been deactivated by means of blocking agents.

The following comparative examples and examples illustrate the invention without restricting it.

All amounts indicated are, unless indicated otherwise, by mass.

The determination of the NCO content of the resins described in the examples and comparative examples was carried out by titration in accordance with DIN EN ISO 11 909.

The phosphorus content was determined by X-ray fluorescence analysis (RFA).

The determination of the residual monomer contents was carried out by gas chromatography in accordance with DIN EN ISO 10283.

The dynamic viscosities were determined at 23° C. using a VT 550 viscometer from Haake. It was ensured by measurements at different shear rates that the flow behavior of the inventive polyisocyanate mixtures described and also that of the comparative products corresponds to that of ideal Newtonian liquids. It is therefore not necessary to report the shear rate.

Mol % figures were determined by NMR spectroscopy and are always based, unless indicated otherwise, on the sum of the NCO subsequent products newly formed in the modification reaction. The measurements were carried out on the instruments DPX 400 and DRX 700 from Bruker using about 5% strength ($^1$H-NMR) and about 50% strength ($^{13}$C-NMR) samples in dry $C_6D_6$ at a frequency of 400 or 700 MHz ($^1$H-NMR) or 100 or 176 MHz ($^{13}$C-NMR). As reference for the ppm scale, small amounts of tetramethylsilane in the solvents were employed and assigned a $^1$H-NMR chemical shift of 0 ppm. Alternatively, the signal of the $C_6D_5H$ present in the solvent was used as reference: $^1$H-NMR chemical shift of 7.15 ppm, $^{13}$C-NMR chemical shift of 128.02 ppm. Data for the chemical shift of the compounds in question were taken from the literature (cf. D. Wendisch, H. Reiff and D. Dieterich, Die Angewandte Makromolekulare Chemie 141, 1986, 173-183, and literature cited therein and also EP 896 009.

All reactions were, unless indicated otherwise, carried out under a nitrogen atmosphere.

The diisocyanates used are products of Bayer MaterialScience AG, D-51368 Leverkusen; all other commercially available chemicals were procured from Aldrich, D-82018 Taufkirchen. The preparation of the hydrogenpolyfluoride catalysts is known from the literature and is described, inter alia, in EP 962 454.

EXAMPLE 1 COMPARATIVE EXAMPLE 1000 g of HDI were placed in a double-walled flange vessel which was maintained by means of an external circuit at 60° C. and provided with stirrer, reflux condenser connected to an inert gas unit (nitrogen/vacuum) and thermometer and freed of dissolved gases by stirring for 1 hour under reduced pressure (0.1 mbar). After admission of nitrogen, 507 mg of a 70% strength isopropanol solution of tetrabutylphosphonium hydrogendifluoride were introduced a little at a time in such a way that the temperature of the reaction mixture did not exceed 65° C. After about 1 mol of NCO groups had reacted, the catalyst was deactivated by addition of an amount of p-toluenesulfonic acid (as 40% strength solution in isopropanol, "stopper solution") equivalent to the catalyst, stirred for a further 30 minutes at the reaction temperature and subsequently worked up. The work-up of the crude solution, whose refractive index measured at 25° C. was at the frequency of the light of the D-line of the Na emission spectrum (in the further text $n_D^{25}$) of 1.4602, was carried out by vacuum distillation in a thin film evaporator, short path evaporator (SPE) type, with upstream preevaporator (PE) (distillation data: pressure: 0.08+/−0.04 mbar, PE temperature: 120° C., SPE temp.: 140° C.), with unreacted monomer being separated off as distillate and the low-monomer polyisocyanate resin being separated off as bottom product (initial pass, example 1-A). The polyisocyanate resin was separated off and the distillate was collected in a second stirred flange apparatus, which had an identical construction to the first, and made up to the initial amount (1000 g) with freshly degassed HDI. Catalysis and the procedure as described at the outset was subsequently carried out again. This procedure was repeated a total of five times with variation of amount of catalyst, conversion and reaction time (for details, see table 1). The phosphorus balance was determined from analysis of the phosphorus contents of the polyisocyanate resins obtained and the recycle monomer remaining at the end of the series of experiments. The total recovery was 92% and 79% of the phosphorus found was in the resins and 21% was in the glass distillate. The data for the polyisocyanate resins obtained in experiments 1-B to 1-F are likewise shown in table 1.

duced into the process, 1b that recovered by distillation). Reservoir 2 contained the catalyst. The streams 1 and 2 were firstly fed to a first mixing element (MI). The streams were brought to the intended temperature by means of heat exchangers (WT) before entry into the first mixing element.

TABLE 1

| Ex. 1 | $Bu_4P^+ HF_2]^-$ solution[a] [mg] | Reaction time [hh:mm] | $n_D^{25}$ [b] | Amount of resin [g] | NCO in resin | Resin viscosity [mPas/23° C.] | Iso-cyan-urates[c] | Iminooxa-diazine-diones[c] | Uret-diones[c] |
|---|---|---|---|---|---|---|---|---|---|
| A | 507 | 00:34 | 1.4602 | 195 | 23.6% | 694 | 50.5 | 44.3 | 5.2 |
| B | 340 | 00:22 | 1.4598 | 198 | 23.5% | 684 | 47.1 | 49.4 | 3.5 |
| C | 214 | 00:30 | 1.4595 | 162 | 23.6% | 680 | 46.3 | 48.6 | 5.1 |
| D | 134 | 00:48 | 1.4590 | 159 | 23.9% | 710 | 65.3 | 32.8 | 1.9 |
| E | 611 | 01:12 | 1.4653 | 300 | 22.8% | 1375 | 56.5 | 38.0 | 5.5 |
| F | 714 | 00:38 | 1.4689 | 391 | 21.5% | 1940 | 44.0 | 51.3 | 4.7 |

[a]70% strength in iPrOH;
[b] refractive index of the reaction mixture after introduction of the stopper before distillation,
[c]mol % according to NMR, based on the sum of the NCO subsequent products formed in the modification reaction.

EXAMPLE 2 COMPARATIVE EXAMPLE

The procedure as described in example 1 was repeated, with the difference that a 0.5% strength solution of benzyltrimethylammonium hydroxide ($BzMe_3N^+OH^-$) in 2-ethylhexanol (ex. 2-A to 2-F) or 2-ethyl-1,3-hexanediol (ex. 2-G to 2-L, for amounts see table 2) was used as catalyst in each case and the stoichiometric amount of dibutyl phosphate (for amounts see table 2) was used as stopper. The analytical data for the polyisocyanate resins obtained in examples 2-A to 2-L, which had a distinctly perceptible amine odor immediately after they had been prepared, are likewise shown in table 2.

The first mixing element was a μ-structured cascade mixer from Ehrfeld Mikrotechnik BTS GmbH.

After intensive mixing of the components, the stream was fed to the reaction section (RS) formed in the present example by a plurality of heat exchangers from Fluitec connected in series. As an alternative, static mixing elements such as Kenics or SMX can also be used here. The temperature of the reaction mixture was maintained at the intended temperature (60+/−0.5° C.) by intensive heat transfer.

After a defined residence distance, a further component was fed to the reaction medium from a reservoir 3 (stopper solution) via a further mixing element (M2). The reaction

TABLE 2

| Ex. 2 | $BzMe_3N^+$ $OH^-$ solution [g] | Dibutyl phosphate [g] | Reaction time [hh:mm] | $n_D^{25}$ [a] | Amount of resin [g] | NCO in resin | Resin viscosity [mPas/23° C.] | Iso-cyan-urates[b] | Iminooxa-diazine-diones[b] | Allo-phanates[b] | Uret-diones[b] |
|---|---|---|---|---|---|---|---|---|---|---|---|
| A | 12.05[c] | 0.08 | 2:22 | 1.4617 | 238 | 22.4% | 1040 | 81.4 | 3.9 | 14.3 | 0.4 |
| B | 15.00[c] | 0.09 | 2:59 | 1.4648 | 298 | 21.9% | 1400 | 83.1 | 2.8 | 13.8 | 0.3 |
| C | 15.20[c] | 0.10 | 2:19 | 1.4702 | 402 | 21.5% | 2240 | 85.2 | 2.1 | 12.5 | 0.2 |
| D | 15.18[c] | 0.10 | 2:42 | 1.4753 | 497 | 21.0% | 4340 | 89.2 | 1.4 | 9.1 | 0.3 |
| E | 20.30[c] | 0.12 | 2:30 | 1.4837 | 604 | 19.6% | 11000 | 89.4 | 1.8 | 8.6 | 0.2 |
| F | 25.05[c] | 0.16 | 3:01 | 1.4911 | 701 | 18.2% | 40000 | 89.7 | 1.3 | 8.6 | 0.4 |
| G | 10.05[d] | 0.07 | 0:04 | 1.4611 | 198 | 22.0% | 2570 | 70.9 | 1.4 | 26.4 | 1.3 |
| H | 10.05[d] | 0.07 | 0:50 | 1.4646 | 296 | 21.9% | 2940 | 78.1 | 1.2 | 18.8 | 1.9 |
| I | 7.63[d] | 0.06 | 1:30 | 1.4685 | 405 | 21.8% | 3610 | 88.2 | 1.5 | 9.4 | 0.9 |
| J | 9.93[d] | 0.07 | 2:09 | 1.4741 | 506 | 21.0% | 6300 | 86.3 | 1.4 | 11.5 | 0.8 |
| K | 13.10[d] | 0.08 | 3:46 | 1.4828 | 598 | 20.0% | 18000 | 87.4 | 1.9 | 9.9 | 0.9 |
| L | 20.00[d] | 0.13 | 4:24 | 1.4903 | 694 | 19.2% | 59000 | 86.0 | 1.6 | 12.0 | 0.4 |

[a] Refractive index of the reaction mixture after introduction of the stopper before distillation,
[b]mol % according to NMR, based on the sum of the NCO subsequent products formed in the modification reaction,
[c]0.5% strength solution in 2-ethylhexanol;
[d]0.5% strength solution in 2-ethyl-1,3-hexanediol

EXAMPLE 3 ACCORDING TO THE INVENTION

A continuously operated setup was operated as described below using (degassed) HDI pretreated in a manner analogous to example 1 and the catalyst and stopper solutions used in example 1.

FIG. 1 schematically shows a setup for carrying out the process of the invention. Four reservoirs 1-a, 1-b, 2 and 3 from which the starting materials were fed separately to the reaction section are present.

The reservoirs 1-a and 1-b contained the monomeric (di)isocyanate to be reacted (1a the monomer freshly intromixture passed through a defined residence distance (Bo about 90) consisting of heat transfer elements before reaching the vessel (4) for intermediates and from there being conveyed to the removal of monomer (by distillation), consisting of a preevaporator and a short path evaporator (5). The unreacted monomer obtained here by distillation was recirculated to 1b (see above) while the low-monomer polyisocyanate was discharged.

The distillation was carried out in the same apparatus as in example 1.

Over 24 h at an average consumption of catalyst solution analogous to ex. 1 of about 300 mg/$kg_{HDI}$ (stopper solution analogous to ex. 1: 305 mg/kg$_{HDI}$), an average of 210 g$_{resin}$/kg$_{HDI}$ of a polyisocyanate resin having the following data (example 3a):
NCO content: 23.5%
Viscosity: 710 mPas/23° C.
Iminooxadiazinediones: 49 mol %*
Isocyanurates: 47 mol %*
Uretdiones: 4 mol %*
*=based on the total NCO subsequent products formed in the modification reaction, were obtained with high consistency.

The amount of catalyst introduced was subsequently reduced stepwise to a minimum 105 mg/kg of HDI. At this setting and a correspondingly adapted introduction of stopper (108 mg/kg$_{HDI}$), an average of 195 g$_{resin}$/kg$_{HDI}$ of a polyisocyanate resin having the following data (example 3b):
NCO content: 23.7%
Viscosity: 710 mPas/23° C.
Iminooxadiazinediones: 45 mol %*
Isocyanurates: 48 mol %*
Uretdiones: 7 mol %*
*=based on the total amount of NCO subsequent products formed in the modification reaction
were formed with high consistency over a further 24 h.

The phosphorus balance was determined from the analysis of the phosphorus contents of the polyisocyanate resins obtained and the recycle monomer remaining at the end of the series of experiments. The total recovery was 96% and 98% of the phosphorus found was present in the resins and 2% was present in the glass distillate, which represents a significant improvement on the result found in comparative example 1.

As a comparison of the result of the abovementioned example 3b according to the invention with the result obtained in comparative example 1d demonstrates, the iminooxadiazinedione group content of the resin from the example according to the invention is significantly increased at a significantly reduced amount of catalyst (relative to the monomer used) and otherwise identical reaction conditions.

EXAMPLE 4 ACCORDING TO THE INVENTION

Using (degassed) HDI pretreated in a manner analogous to example 2 and the catalyst solution used in examples 2-A to 2-F and also dibutyl phosphate as stopper (as 10% strength solution in 2-ethylhexanol), a polyisocyanate resin having the following data:
Resin yield (based on HDI used): 21.8%
NCO content: 23.2%
Viscosity: 1250 mPas/23° C.
Iminooxadiazinediones: 3 mol %*
Isocyanurates: 88 mol %*
Uretdiones: 3 mol %
Allophanates: 6 mol %
*=based on the total NCO subsequent products formed in the modification reaction, was obtained with high consistency over 24 h at an average catalyst consumption of about 4.5 g/kg$_{HDI}$ (stopper solution corresponding to 285 mg/kg$_{HDI}$) in an apparatus as described in example 3.

No amine odor was perceptible even immediately after removal of the resin from the distillation apparatus.

EXAMPLE 5 COMPARATIVE EXAMPLE

Using (degassed) HDI pretreated in a manner analogous to example 1 and the catalyst and stopper solutions used in example 1, the following data:

Resin yield (based on HDI used): 18.1%
NCO content: 22.8%
Viscosity: 1030 mPas/23° C.
Iminooxadiazinediones: 42 mol %*
Isocyanurates: 55 mol %*
Uretdiones: 4 mol %
were obtained in an apparatus analogous to example 3 but at a deliberately broadened residence time distribution (Bo about 30, i.e. reduced by a factor 3 compared to example 3).

EXAMPLE 6 ACCORDING TO THE INVENTION

Using the apparatus analogous to that used in example 3 and an amount of catalyst (based on monomer) increased by a factor of 6 compared to example 3a and nevertheless very good temperature control (temperature increase <1 K), the space-time yield was increased by a factor of 5 and a polyisocyanate resin having the following data:
Resin yield (based on HDI used): 29.5%
NCO content: 22.3%
Viscosity: 1120 mPas/23° C.
Iminooxadiazinediones: 48 mol %*
Isocyanurates: 47 mol %*
Uretdiones: 5 mol %
was obtained.

The refractive index of the stopped crude product ($n_D^{25}$) before distillation was on average 1.4658.

Comparison of examples 1-A to 1-F and of example 6 with the examples of HDI trimerization reported in EP 17998 demonstrates a significantly lower NCO content in the low-monomer polyisocyanates as per EP 17998 (from 20.9 to 21.4%) relative to the monomer conversion (indicated by the refractive index of the crude product ($n_D^{25}$)—in EP 17998 in the range from 1.4658 to 1.4676).

It can immediately be seen therefrom that the teaching of EP 17998 makes it possible to obtain only products having a significantly broader molecular weight distribution than in a batch experiment and in the process according to the invention.

The invention claimed is:

1. A process for the continuous preparation of oligomeric or polymeric isocyanates by catalytic modification of monomeric diisocyanates and/or triisocyanates, comprising continuously combining at least one isocyanate component A and at least one catalyst component B in a reaction apparatus and conveying as reaction mixture through the reaction apparatus, wherein a residence time distribution according to the dispersion model has a Bo (Bodenstein number) above 40 and wherein the residence section has a maximum pressure drop of from 0 to 30 bar and has a heat transfer rate above 10 kW/(K m3).

2. An oligomeric or polymeric isocyanate obtained by the process as claimed in claim 1.

3. A method for producing optionally foamed plastics and surface coatings, coating compositions, adhesives and auxiliaries comprising utilizing the oligomeric or polymeric isocyanates as claimed in claim 2.

4. The process according to claim 1, wherein the catalyst is used in a proportion of from 5 mol-ppm to 0.1 mol %, based on the mass of diisocyanate and/or triisocyanate used.

5. The process according to claim 1, wherein the isocyanate component and the catalyst component are combined using an intensive mixer.

6. The process according to claim 1, wherein not only the components A and B but also further compounds are present in the reaction mixture or these are introduced along the reaction section, where these are, in the first case, bonding agents, stabilizers or fluidizers and in the second case, bonding agents, stabilizers, fluidizers, diisocyanates or triisocyanates different from A, catalysts different from B or catalyst-deactivating materials.

7. The process according to claim 1, wherein intensive mixing of all components is effected by use of mixing elements along the residence section.

8. The process according to claim 1, wherein it is carried out in the temperature range from 0° C. to +200° C., with a constant reaction temperature being realized over the entire reaction region.

9. The process according to claim 1, wherein pentane 1,5-diisocyanate, hexamethylene diisocyanate (HDI), 2-methylpentane 1,5-diisocyanate, 2,4,4-trimethylhexane 1,6-diisocyanate, 2,2,4-trimethylhexane 1,6-diisocyanate, 4-isocyanatomethyloctane 1,8-diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)cyclohexane (H6XDI), tolylene 2,4- and 2,6-diisocyanate (TDI), bis(4-isocyanatophenyl)methane (4,4'-MDI), 4-isocyanatophenyl-2-isocyanatophenylmethane (2,4'-MDI) and/or multi-ring products which can be obtained by formaldehyde-aniline polycondensation and subsequent conversion of the resulting (poly)amines into the corresponding (poly)isocyanates (polymeric MDI) are used as diisocyanates and/or triisocyanates.

10. The process according to claim 1, wherein aliphatic diisocyanates and/or triisocyanates are used.

11. The process according to claim 1, wherein
tetraorganylammonium and/or tetraorganylphosphonium salts whose anions are derived by H+ abstraction from weak acids selected from the group consisting of carboxylic acids, carboxylic acids bearing fluorinated alkyl groups, phenols, alcohols, water and HF, in solid or dissolved form,
alcoholic solutions of alkali metal and alkaline earth metal oxides, hydroxides, alkoxides and phenoxides,
alcoholic solutions of metal salts of carboxylic acids, selected from the group consisting of potassium acetate, sodium benzoate, sodium acetate and potassium formate and/or
tertiary phosphines which contain the phosphorus atom as part of a ring, in solid or dissolved form,
are used as catalysts.

12. The process according to claim 1, wherein the catalyst is used in a proportion of from 1 mol-ppm to 1 mol %, based on the mass of diisocyanate and/or triisocyanate used.

13. The process as claimed in claim 1, wherein the process is stopped after from 5 to 80% of the monomeric diisocyanate and/or triisocyanate used has been reacted.

14. The process according to claim 1, wherein the catalyst is used in a proportion of from 5 mol-ppm to 0.1 mol %, based on the mass of diisocyanate and/or triisocyanate used.

* * * * *